United States Patent [19]

Tarral et al.

[11] Patent Number: 4,824,664
[45] Date of Patent: Apr. 25, 1989

[54] EFFERVESCENT COUPLES, HISTAMINE $H_2$-ANTAGONIST EFFERVESCENT COMPOSITIONS CONTAINING THEM AND THEIR PREPARATION

[75] Inventors: René Tarral, Paris; Jacky Mention, Leognan, both of France

[73] Assignee: Laboratoires Smith Kline & French, Paris, France

[21] Appl. No.: 4,725

[22] Filed: Jan. 20, 1987

[30] Foreign Application Priority Data

Jan. 22, 1986 [FR] France ............................ 8600839

[51] Int. Cl.⁴ .................... A01N 25/02; A61L 9/04
[52] U.S. Cl. ................................ 424/43; 424/44; 424/439; 424/446
[58] Field of Search ............ 424/43, 44, 939, 466

[56] References Cited

U.S. PATENT DOCUMENTS

| | | | |
|---|---|---|---|
| 1,764,996 | 6/1930 | Andrews | 424/44 |
| 2,147,743 | 2/1939 | Levin | 424/44 |
| 3,887,700 | 6/1975 | Boncey et al. | 424/44 |
| 4,289,751 | 9/1981 | Windhevser | 424/44 |
| 4,503,051 | 3/1985 | Algieri et al. | 514/326 |
| 4,522,943 | 6/1985 | Algieri et al. | 514/318 |
| 4,537,900 | 8/1985 | Kreidl et al. | 514/400 |

FOREIGN PATENT DOCUMENTS

| | | | |
|---|---|---|---|
| 682873 | 12/1966 | Belgium | 424/44 |
| 749864 | 10/1970 | Belgium | 424/44 |

*Primary Examiner*—Ellis P. Robinson
*Assistant Examiner*—P. J. Ryan
*Attorney, Agent, or Firm*—Joseph A. Marlino; Stuart R. Suter; Alan D. Lourie

[57] ABSTRACT

The invention relates to an effervescent couple which comprises a mixture of mono-and di-alkali metal citrate as well as to a process for preparing same. The process comprises partially neutralizing citric acid by reacting an alkali metal carbonate or bicarbonate with citric acid and water and controlling the amount of carbon dioxide released during the reaction by stopping the reaction when a certain amount of citric acid has been neutralized. In a preferred embodiment the reaction is stopped when from about 24% to about 54% of the potential amount of carbon dioxide has been released.

16 Claims, No Drawings

EFFERVESCENT COUPLES, HISTAMINE $H_2$-ANTAGONIST EFFERVESCENT COMPOSITIONS CONTAINING THEM AND THEIR PREPARATION

This invention relates to effervescent couples, histamine $H_2$-antagonist effervescent compositions containing them and their preparation. These compositions are formulated as powders and tablets which dissolve with effervescence.

Histamine, a physiologically active compound, endogenous in mammals, exerts its action by interacting with certain sites called receptors. One type of receptor is known as a histamine $H_1$-receptor (Ash and Schild, Brit. J. Pharmac. Chemother. 27 427 (1966)) and the actions of histamine mediated through these receptors are blocked by drugs commonly called "antihistamines" (histamine $H_1$-antagonists) a common example of which is mepyramine. A second type of histamine receptor is known as the $H_2$-receptor (Black et al., Nature 1972, 236, 385). These receptors are not blocked by mepyramine but are blocked by burimamide. Compounds which block these histamine $H_2$-receptors are called histamine $H_2$-antagonists.

As classical histamine $H_2$-antagonists cimetidine, famotidine, ranitidine, nizatidine, etintidine, lupitidine, mifentidine, niperotidine, roxatidine, sufotidine, tuvatidine and zaltidine may be cited.

These products are useful in the treatment of ulcerations of gastroduodenal mucosa (duodenal ulcer, benign gastric ulcer, recurrent ulcer and post surgical peptic ulcer), peptic oesophagitis, haemorrhages resulting from oesophageal, gastric or duodenal ulcerations or erosions and Zollinger-Ellison syndrome.

In patients having recurrent duodenal ulceration antecedents they are useful for preventing recurrence.

For oral administration, histamine $H_2$-antagonists can be formulated in tablets or aqueous supension form.

So, European patent application publication EP No. 0 138 540 discloses compositions for oral administration of cimetidine which are formulated as optionally flavored aqueous suspensions for attenuating bitterness of the compound; these compositions may also contain an antacid, i.e. a pharmaceutically acceptable compound of alkaline nature and being able, as, for example, calcium carbonate, to neutralize gastric acidity.

Contrary to the previously known pharmaceutical forms for oral administration of histamine $H_2$-antagonists and among them those of European patent application publication EP No. 0 138 540, the compositions of this invention are not administered as such, but they are extemporaneously poured into an aqueous carrier (for example, drinking water) in which they are effervescent, leading to a rapid dissolution of the histamine $H_2$-antagonist compound. According to a preferred embodiment, the pharmaceutical compositions of this invention form limpid solutions which can be easily flavored and present a particularly pleasant formulation.

The compositions of this invention are characterized by a particularly good stability during storage and a complementary antacid potential. Since they are not limited to volume requirement as it is more particularly the case for crunchable or swallowable tablets, pharmaceutical compositions of this invention can also contain significant amount of antacid, such as, for example, aluminum or magnesium hydroxide or an alkali metal or alkali earth metal carbonate or bicarbonate, preferably, alkali metal bicarbonate. It has been noticed, indeed, that, when compared to classical tablet formulation, effervescent compositions of this invention containing an alkali metal bicarbonate do not modify the bioavailability of $H_2$-antagonist but provokes the acceleration of its absorption.

Thus, the effervescent form of the invention allows to reach efficient plasma levels much more rapidly than the standard tablet form without any statistically significant decrease of bioavailability.

In order to compare the relative bioavailability of classical tablets and effervescent tablets prepared according to the present invention, tablets dosing 800 mg of cimetidine were used which were administered in two distinct passages to 12 patients for 4 consecutive days. These patients were of both sexes, they were 25 years ($\pm 1$ year) of average age, their weight was 62 kg ($\pm 3$ kg) and, a pre-trial testing of their blood revealed no anomaly.

At a 10 days interval, the patients were given a treatment with classical tablets and a treatment with effervescent tablets.

In each case, administration was carried out at 19 hours in the middle of evening meal, this latter consisting of vegetable soup, 2 hard-boiled eggs with mayonnaise, green salad and fruit salad.

Cimetidine has been measured out of plasma and urine of patients by high performance liquid chromatography.

In plasma, although Cmax mean values (characteristics of plasma level peak observed after the first and fourth administration of both tablet forms) are close (they only differ from 3% and 8% at day 1 and day 4), analyses showed that mean values of cimetidine plasma levels ($\mu g/ml^{-1}$), measured during the first hour after the first and the fourth administration of effervescent tablet and depicted in the following Table, are significantly higher than those observed after absorption of standard tablet.

| Time (h) | Standard tablet | | Effervescent tablet | |
|---|---|---|---|---|
| | 1st day | 4th day | 1st day | 4th day |
| 0.25 | 0.053 | 0.135 | 1.791 | 1.600 |
| | (0.026) | (0.091) | (0.242) | (0.382) |
| 0.50 | 0.492 | 0.312 | 3.176 | 2.506 |
| | (0.146) | (0.148) | (0.376) | (0.345) |
| 0.75 | 1.532 | 0.937 | 3.088 | 2.459 |
| | (0.515) | (0.332) | (0.322) | (0.224) |
| 1.00 | 2.071 | 1.372 | 3.042 | 2.312 |
| | (0.362) | (0.427) | (0.248) | (0.183) |

N.B. Values indicated between brackets are standard deviation values

Thus, the effervescent tablet form of the invention allows to reach efficient plasma levels more quickly than the classical tablet form without any statistically significant decrease of bioavailability.

In urine, the total amount of cimetidine excreted between 0 and 24 hours and between 27 and 96 hours has been shown practically identical for both types of tablets.

Depending on whether the composition is formulated in powder or tablet form, it will also be able to contain various additives as it is well known to the art; such additives are binding and lubricating agents (for example, polyvinylpyrrolidone, sodium benzoate, polyethylene glycol, L-leucine or laurylmagnesium sulfate) and flavoring and coloring agents; among them, siliconized sodium benzoate, considered here as lubricating agent, has been shown particularly attractive.

The principles for preparing pharmaceutical effervescent compositions are known (see for example Pharmaceutical Dosage Forms (Tablets/Vol. 1) by Lieberman H. A. and Lachman L., M. Dekker editions New York, 1980, chapter 5, Effervescent Tablets by R. Mohrle p. 255-258) and various techniques have been described for improving stability of compositions or means for preparing thereof. For instance French Pat. No. 1 484 202 describes a process of preparation of an acidic compound for effervescent compositions characterized by the fact that an organic polyacid is allowed to react in powder form with sodium bicarbonate in an amount less than the stoichiometric amount required for complete neutralization of the organic polyacid;

U.S. Pat. No. 2,984,543 discloses a process for stabilizing bicarbonate effervescent compositions in powder form wherein the carbon dioxide-generating compound (i.e. a carbonate or bicarbonate in finely divided form) is impregnated with a mucilage or a natural or synthetic hydrophilic gum solution;

U.S. Pat. No. 2,985,562 discloses a process for improving free-flowing characteristics of effervescent compositions by addition of a small quantity of a monocarboxylic amino acid followed by a thermal treatment between 60° and 120° C.;

U.S. Pat. No. 3,105,792 discloses a process for improving physical characteristics of effervescent tablets by a preliminary thermic treatment of the bicarbonate, during which treatment the bicarbonate particles surface is transformed into corresponding carbonate;

U.S. Pat. No. 3,875,073 claims the addition of a protein for stabilizing effervescent mixtures against moisture;

U.S. Pat. Nos. 3,773,922 and 3,946,996, PCT patent application 84/02 468 and Belgian Pat. No. 781 358 disclose various devices or processes for preparing effervescent tablets or granules;

Belgian Pat. No. 760 288 discloses effervescent powders and tablets prepared from carbonate or bicarbonate and acid where the acid component is constituted by pure sodium dihydrogen citrate;

European Pat. No. 0 011 489 discloses a process for preparing an analgesic effervescent powder characterized in that the effervescent forming material is either sodium dihydrogen citrate or disodium hydrogen citrate;

European Pat. No. 0 076 340 claims a method for the preparation of effervescent granules allowing to carry out a passivation of the surface of the granules by a process comprising several repetitive steps;

French patent application published under No. 2 552 308 claims an effervescent mixture formed by cristallized solid organic acid and a carbon dioxide source and wherein the acid cristals present a protective coating containing calcium carbonate;

British patent applications Nos. 2 091 625, 2 093 052 and 2 093 376 disclose different variations of an apparatus allowing the preparation of effervescent granules and the treatment of their surface for increasing their resistance to moisture.

It has now been noticed that the preparation of effervescent compositions from a mixture of an histamine $H_2$-antagonist (cimetidine), a carbon dioxide source (sodium bicarbonate) and an acid (citric acid) presented a particular problem due to the instability of histamine $H_2$-antagonist in presence of acid and that the substitution of sodium dihydrogen citrate for citric acid does not satisfactorily improve histamine $H_2$-antagonist stability whereas the substitution of disodium hydrogen citrate for citric acid strongly decreased effervescence of the solution and the solubility of histamine $H_2$-antagonist.

Nevertheless, and this is the object of the present invention, it has been found possible to maintain an acceptable effervescence level without harming histamine $H_2$-antagonist stability provided that citric acid be present as a sodium or potassium dihydrogen citrate/disodium or dipotassium hydrogen citrate couple in a weight ratio comprised between 8/1 and 1/10 and preferably comprised between 2/1 and 6/10.

For instance, when preparing an effervescent cimetidine tablet containing citric acid, immediate degradation of the cimetidine is noticed and, when pure monosodium citrate is substituted for citric acid, a 38% degradation is noticed after one week at 70° C. whereas, in the same conditions, no degradation is detected with a couple according to the present invention.

The notion of "couple" is herein defined as the product obtained by wet granulation followed by drying of a mixture of a polycarboxylic acid and an alkaline carbon dioxide source in an amount at least stoichiometric in relation to acidity of the medium but in such operating conditions that acid is partially neutralized.

Thus, the couples according to the invention are antacid effervescent couples prepared from a pharmaceutically acceptable polycarboxylic acid and a carbon dioxide source characterized in that they comprise sodium or potassium dihydrogen citrate and disodium or dipotassium hydrogen citrate in a weight/weight ratio comprised between 8/1 and 1/10, preferably between 2/1 and 6/10.

For couples prepared from stoichiometric amounts of citric acid and sodium bicarbonate, such result is reached by stopping the reaction when from 24 to 54% of the potential amount of carbon dioxyde has been released.

It is obvious that the couples may also contain different additives in the same way as final compositions, as indicated hereinabove. Among these additives, benzoate, in the form of a micronized and siliconized alkaline benzoate, has been found particularly valuable.

Incidentally it will be noticed that, in the prior art, those skilled in the art were concerned mainly with the stability of the acid/carbon dioxide source couple itself in presence of moisture whereas, in the present invention, the first objective was to stabilize also the medically active ingredient.

The invention is illustrated by the following examples which are not limiting its scope.

EXAMPLE 1

In a drier granulator blender comprising a thermostatable jacketed vessel connected to a vacuum pump, an aperture for charging solid materials, an aperture for introducing liquids in dispersed form, a mixing device assuring a thorough homogeneity and an atmospheric pressure outlet device and heated to 100° C. ($\pm 5°$ C.), 43.250 kg of powdered anhydrous citric acid and 56.750 kg of sodium bicarbonate are introduced through a one millimeter opening grid sieve. The mixture is heated under vigorous stirring. When the temperature of the products reaches 40° C. ($\pm 1°$ C.), the thermostat of the jacket is set on 75° C. ($\pm 1°$ C.).

When the temperature of the mixture reaches 45° C. (±1° C.), water (160 ml) is introduced under reduced pressure (600 mm Hg) and the atmospheric pressure outlet device is opened. The mixture is allowed to react for 40 minutes under vigorous stirring. Stirring speed is then reduced and the reaction is stopped by drying under vigorous and continuous suction provoking a decrease of residual pressure and temperature (about 5° to 10° C.), this latter rising again as soon as the mass is dry.

Vacuum is then relieved and the mass is calibrated through a two millimeters opening grid sieve.

A stoichiometric couple (78.5 kg) having a 64.2% effervescent activity (expressed in percentage of carbon dioxide initial potential) corresponding to a composition of 32.2% sodium dihydrogen citrate, 31.4% disodium hydrogen citrate and 36.4% sodium bicarbonate is obtained, all percentages being weight/weight and the carbon dioxide dosage being carried out by volumetry based on standardization determined with known amounts of citric acid and sodium bicarbonate.

EXAMPLE 2

In a monitored temperature and relative humidity atmosphere, 20° C. (±2° C.) and 20% (±1%) relative humidity respectively, one kg of cimetidine, 15 kg of the couple obtained at the end of example 1 and 700 g of micronized sodium benzoate are thoroughly mixed.

The mixture is compressed under alternative press equipped with 20 mm diameter round flat stamps of 1.670 g weight to yield tablets at a 100 mg cimetidine dosage.

Tablets are packaged in bags formed by sealing of Kraft/polyethylene (12.5 g)/aluminum (30 μm)/polyethylene (25 g) complex sheets.

In order to determine the stability of tablets, sheets have been stored for 7 days in drying oven at 70° C. (±1° C.) and for 10 days in drying oven at 60° C. (±1° C.) and, by high performance liquid phase chromatography (HPLC) on a Partisil ®-10-SCX column (a cation exchange resin manufactured and sold by Whatman Inc., Clifton, N.J., U.S.A.) using as mobile phase a mixture of ammonium sulfate 0.075M (65 volumes); spectroscopy grade methanol (35 volumes); ammonia qsp pH 7, the eventual presence of cimetidine degradation products, namely N-carbamyl-N'-methyl-N'-[2-(5-methyl-4-imidazolylmethylthio)ethyl]-guanidine and N-methyl-N'-[2-(5-methyl-4-imidazolylmethylthio)ethyl]-guanidine has been investigated. In these conditions, no trace of cimetidine degradation products has been detected showing thus the complete stability of tablets. On the other hand, the manufacture of tablets from a simple mixture of cimetidine (1 kg), sodium benzoate (700 g) and a mixture having an effervescent (63.2%) activity identical to that of the couple obtained at the end of example 1 and consisting of sodium dihydrogen citrate (4.575 kg), disodium hydrogen citrate (5.040 kg) and sodium bicarbonate (5.385 kg) in the same conditions of compression and storage showed a 5.8% content of N-carbamyl-N'-methyl-N'-[2-(5-methyl-4-imidazolylmethylthio)ethyl]-guanidine and a 0.5% content of N-methyl-N'-[2-(5-methyl-4-imidazolylmethylthio)ethyl]-guanidine after 7 days at 70° C. and a content of 8.5% of N-carbamyl-N'-methyl-N'-[2-(5-methyl-4-imidazolylmethylthio)ethyl]-guanidine and a 0.6% content of N-methyl-N'-[2-(5-methyl-4-imidazolylmethylthio-ethyl]-guanidine after 10 days at 60° C.

EXAMPLE 3

In a drier granulator blender comprising a thermostatable jacketed vessel connected to a vacuum pump, an aperture for charging solid materials, an aperture for introducing liquids in dispersed form, a mixing device assuring a through homogeneity and an atmospheric pressure outlet device and heated to 100° C. (±5° C.), 33.560 kg of powdered anhydrous citric acid and 44.040 kg of sodium bicarbonate are introduced through a one millimeter opening grid sieve. The mixture is heated under vigorous stirring. When the temperature of the products reaches 43° C. (±1° C.), the thermostat of the jacket is set on 65° C. (±1° C.).

When the temperature of the mixture reaches 51° C. (±1° C.), water (165 ml) is introduced under reduced pressure (600 mmg Hg) and atmospheric pressure outlet device is opened. The mixture is allowed to react for 35 minutes under vigorous stirring. Stirring is then reduced and the reaction is stopped by drying under vigorous and continuous stirring.

When the mass is dry, vacuum is relieved and the mass is calibrated through a two millimeters opening grid sieve.

A stoichiometric couple (61.2 kg) having a 67,8% effervescent activity (expressed in percentage of carbon dioxide initial potential) corresponding to a composition of 38.6% sodium dihydrogen citrate, 22.9% disodium hydrogen citrate and 38.5% sodium bicarbonate is obtained, all percentages being expressed in weight/weight and carbon dioxide dosage being carried out by volumetry based on standardization determined with known amounts of citric acid and sodium bicarbonate.

EXAMPLE 4

Using the technique described in example 2, cimetidine tablets were prepared with the couple prepared in example 3 and the stability in bags has been tested.

After a 7 days storage at 70° C. (±1° C.), no trace of cimetidine degradation products (N-carbamyl-N-methyl-N'-[2-(5-methyl-4-imidazolylmethylthio)ethyl]-guanidine and N-methyl-N'-[2-(5-methyl-4-imidazolylmethylthio)ethyl]-guanidine respectively) has been detected by high performance liquid chromatography (HPLC).

EXAMPLE 5

In a drier granulator blender comprising a warm water circulating jacketed vessel having a 130 l total capacity (useful capacity: 90 l) connected to a vacuum pump and comprising an aperture for charging solid materials, a aperture for introducing liquids in dispersed form, a mixing device assuring a thorough homogeneity, a high speed rotary cutter and an atmospheric pressure outlet device and heated at 65° C., 20.975 kg of powdered anhydrous citric acid, 27.525 kg of sodium bicarbonate and 1.500 kg of polyethylene glycol (molecular weight: 6000) are introduced under vigorous stirring through a one millimeter opening grid sieve. The mass is broken with the rotary cutter and then heated under vigorous stirring. When the temperature of the mixture reaches 51° C., water (300 ml) is added thereto in six equal portions, at 3 minutes interval, and the mixture is allowed to react under vigorous stirring for 31 minutes from the first addition of water.

The reaction is stopped by drying under vigorous and continuous suction, homogeneity of the mass being maintained by using mixing device at low speed and on discontinuous schedule.

After drying, 39.200 kg of the stoichiometric couple are obtained. This couple has a 70.3% effervescent activity (expressed in percentage of carbon dioxide initial potential) corresponding to a composition of 42.4% sodium dihydrogen citrate, 15.5% disodium hydrogen citrate, 38.65% sodium bicarbonate and 3.2% polyethylene glycol, all percentages being in weight/weight and carbon dioxide dosage being carried out by volumetry based on standardization determined with known amounts of citric acid and sodium bicarbonate.

EXAMPLE 6

Using the technique described in example 2, cimetidine tablets were prepared with the couple prepared in example 3 and stability in bags has been tested.

After a 20 days of storage at 40° C. (±1° C.), no trace of degradation products (N-carbamyl-N'-methyl-N'-[2-(5-methyl-4-imidazolylmethylthio)ethyl]-guanidine and N-methyl-N'-[2-(5-methyl-4-imidazolylmethylthio)ethyl]-guanidine, respectively) has been detected by high performance liquid chromatography (HPLC).

EXAMPLE 7

In order to determine acceptability limits of cimetidine-based effervescent compositions, a couple having an effervescent activity higher than that of the preceding examples was prepared. To this end, the procedure described in example 1 was followed but reducing reaction time from 40 minutes to 25 minutes.

A stoichiometric couple (85 kg) having a 78% effervescent activity has been obtained and this couple has been used for preparing cimetidine tablets following the procedure of example 2.

Stability test showed a significant degradation of cimetidine in N-carbamyl-N'-methyl-N'-[2-(5-methyl-4-imidazolylmethylthio)ethyl]-guanidine (0.89%) at the end of tablet manufacture and 6% after a one week storage at 70° C. (±1° C.).

Moreover, a stability test of tablets prepared according to the procedure of example 2 from cimetidine (1 kg), sodium benzoate (700 g) and a mixture of sodium dihydrogen citrate (8.405 kg) and sodium bicarbonate (6.595 kg) and having the same effervescent activity as the couple prepared hereinabove (78%), showed, after 7 days at 70° C., a degradation product content of 38% in N-carbamyl-N'-methyl-N'-[2-(5-methyl-4-imidazolylmethylthio)ethyl]-guanidine and 4% in N-methyl-N'-[2-(5-methyl-4-imidazolylmethylthio)ethyl]-guanidine, and, after 10 days at 50° C., a content of 4% in N-carbamyl-N'-methyl-N'-[2-(5-methyl-4-imidazolylmethylthio)ethyl]-guanidine.

EXAMPLE 8

The technique is that of example 4 but the same quantity of siliconized sodium benzoate supplemented with 10% of silicone oil (50 centistokes) was substituted for the sodium benzoate of example 2. In this way, tablets were obtained showing no degradation after 7 days at 70° C. nor after 10 days at 60° C.

EXAMPLE 9

The limited protective effect of siliconized benzoate has been examined on tablets obtained with the sodium dihydrogen citrate/sodium bicarbonate mixture of example 7.

To this end, following the procedure of example 2, but replacing the couple and sodium benzoate indicated therein by the same respective amounts of the sodium dihydrogen citrate/sodium bicarbonate mixture and siliconized sodium benzoate supplemented with 10% of silicone oil (50 centistokes), cimetidine base tablets were prepared whose stability has been tested after storage for 7 days at 70° C. In these conditions, the N-carbamyl-N'-methyl-N'-[2-(5-methyl-4-imidazolylmethylthio)ethyl]-guanidine content was reduced from 38% to 12% and the N-methyl-N'-[2-(5-methyl-4-imidazolylmethylthio)ethyl]-guanidine content was reduced from 4% to 1,2%.

The limited protective effect of siliconized sodium benzoate has also been examined on tablets obtained by the procedure of example 2 using the sodium dihydrogen citrate/disodium hydrogen citrate/sodium bicarbonate mixture indicated in example 2. It has then been observed that, after a 10 days storage at 60° C., N-carbamyl-N'-methyl-N'-[2-(5-methyl-4-imidazolylmethylthio)ethyl]-guanidine and N-methyl-N'-[2-(5-methyl-4-imidazolylmethylthio)ethyl]-guanidine levels were reduced from 8.5% to 6.3% and from 0.6% to 0.2%, respectively, after 10 days of storage at 60° C.

EXAMPLE 10

In a drier granulator blender comprising a thermostable jacketed vessel connected to a vacuum pump, an aperture for charging solid materials, an aperture for introducing liquids in dispersed form, a mixing device assuring a thorough homogeneity and an atmospheric pressure outlet device and heated at 100° C., 33.560 kg of powdered anhydrous citric acid and 44.040 kg of sodium bicarbonate are introduced through a one millimeter opening grid sieve and the mixture is heated under vigorous stirring. When the temperature of the products reaches 43° C. (±1° C.), the thermostat of the jacket is set on 65° C. (±1° C.).

When the temperature of the mixture reaches 51° C. (±1° C.), addition of water in pulverized form is carried out by the addition of two 155 ml fractions, at a 5 minutes interval, and, while maintaining a vigorous stirring, the mixture is allowed to react for 50 minutes (measured from the first addition).

Stirring speed is then reduced and the reaction is stopped by drying under vigorous suction, provoking a decrease of residual pressure and temperature (about 5 to 10° C.), this latter rising again, as soon as the mass is dry.

A stoichiometric couple (57.7 kg) having a 59% effervescent activity corresponding to a composition of 23.1% sodium dihydrogen citrate, 43.4% disodium hydrogen citrate and 33.5% sodium bicarbonate is obtained.

EXAMPLE 11

In normal room conditions (26° C. and 50–55% relative humidity), 2.500 kg of cimetidine and 25 kg of the couple obtained at the end of example 10 are thoroughly mixed and the mixture is distributed into bags formed by sealing of Kraft complex sheets 50 g, polyethylene 12.5 g, aluminum 30 μm and polyethylene 25 g.

In order to test the stability of the so packaged powder, bags have been stored for 6 weeks in drying oven at 50° C. (±1° C.). After this period, no degradation product has been detected by high performance liquid chromatography whereas in the same storage conditions, a bagged mixture of cimetidine (2.5 kg), powdered anhydrous citric acid (10.815 kg) and sodium bicarbonate (14.185 kg) showed a 0,5% N-methyl-N'-[2-(5-methyl-4-imidazolylmethylthio)ethyl]-guanidine level.

In the same storage conditions, a mixture of cimetidine (2.5 kg), sodium dihydrogen citrate (12.058 kg) and sodium bicarbonate (9.456 kg) showed a 2.3% N-carbamyl-N'-methyl-N'-[2-(5-methyl-4-imidazolylmethylthio)ethyl]-guanidine level and 0.02% N-methyl-N'-[2-(5-methyl-4-imidazolylmethylthio)ethyl]-guanidine level.

EXAMPLE 12

In a drier granulator blender comprising a thermostatable jacketed vessel connected to a vacuum pump, an aperture for charging solid materials, an aperture for introducing liquids in dispersed form, a mixing device assuring an thorough homogeneity and an atmospheric pressure outlet device and heated to 100° C., 36.750 kg of powdered anhydrous citric acid and 63.250 kg of sodium bicarbonate are introduced through a one millimeter opening grid sieve and the mixture is heated under vigorous stirring. When the temperature of the products reaches 40° C., the thermostat of jacket is set on 75° C. When the temperature of the mixture reaches 45°-46° C., water (160 ml) in pulverized form is added under a vigorous stirring. The mixture is allowed to react for 30 minutes (±3 mn). Stirring speed is then reduced and reaction is stopped by drying under vigorous suction provoking a decrease of residual pressure and temperature (about 5° to 10° C.), this latter rising again as soon as the mass is dry.

At this time, vacuum is relieved and the mass is calibrated by passage through a two millimeters opening grid sieve.

A couple (78.4 kg) with an excess of bicarbonate and having a 60.5% effervescent activity and corresponding to a composition of 24.45% sodium dihydrogen citrate, 28.05% disodium hydrogen citrate and 47.5% sodium bicarbonate is obtained.

EXAMPLE 13

Using the technique of example 2, cimetidine tablets with the couple of Example 12 were prepared and the stability in bags has been tested.

After a 13 days storage at 60° C. (±1° C.), 0.3% of N-carbamyl-N'-methyl-N'-[2-(5-methyl-4-imidazolylmethylthio)ethyl]-guanidine was detected by high performance liquid chromatography.

On the other hand, in the same storage conditions, tablets prepared by mixing cimetidine (1 kg) and sodium benzoate (700 g) with a mixture having an effervescent activity identical to that of the preceding couple and consisting of sodium dihydrogen citrate (3.740 kg), disodium dihydrogen citrate (4.12 kg) and sodium bicarbonate (7.140 kg) showed a degradation level of 10.1% in N-carbamyl-N'-methyl-N'-[2-(5-methyl-4-imidazolylmethylthio)ethyl]-guanidine and 1.38% in N-methyl-N'-[2-(5-methyl-4-imidazolylmethylthio)ethyl]-guanidine.

EXAMPLE 14

In a drier granulator blender comprising a thermostatable jacketed vessel connected to a vacuum pump, an aperture for charging solid materials, an aperture for introducing liquids in dispersed form, a mixing device assuring a thorough homogeneity and an atmospheric pressure outlet device and heated to 100° C., (±5° C.), 43.250 kg of powdered anhydrous citric acid and 56.750 kg of sodium bicarbonate are introduced through a one millimeter opening grid sieve. The mixture is heated under vigorous stirring. When the temperature of the products reaches 40° C., the thermostat of the jacket is set on 75° C. When the temperature of the mixture reaches 45°-46° C. and the temperature of the jacket is 75° C., pulverized water (160 ml) is added under vigorous stirring. The mixture is allowed to react for 40 minutes. Stirring speed is then reduced and the reaction is stopped by drying under vigorous suction, provoking a decrease of residual pressure and temperature (about 5° to 10° C.), this latter rising again as soon as the mass is dry. At this moment, vacuum is relieved and the mass is calibrated through a two millimeters opening grid sieve.

A stoichiometric couple (78.600 kg) having a 62% effervescent activity and corresponding to a composition of 28.8% sodium dihydrogen citrate, 35.8% disodium hydrogen citrate and 35.4% sodium bicarbonate is obtained.

EXAMPLE 15

In room conditions controlled for temperature (20° C.) and relative humidity (20%), cimetidine hydrochloride (1.1445 part) is throughly mixed with 15 parts of the couple obtained in example 14 and the mixture is distributed into bags formed by sealing of Kraft complex sheets 50 g, polyethylene 12.5 g, aluminum 30 μm and polyethylene 25 g.

In order to test the stability of the so-packaged powder, bags have been stored for one week at 60° C. and, after that period, no degradation product has been detected by high performance liquid chromatography.

In the same storage conditions, a mixture of
1.1455 parts of cimetidine hydrochloride,
8.5125 parts of cimetidine hydrochloride,
6.4875 parts of powdered anhydrous citric acid,
showed, after one week at 60° C. a 59.6 level of N-carbamyl-N'-methyl-N'-[2-(5-methyl-4-imidazolylmethylthio)ethyl]-guanidine and 3.5% level of N-methyl-N'-[2-(5-methyl-4-imidazolylmethylthio)ethyl]-guanidine.

In the same storage conditions, a mixture of
1.1455 parts of cimetidine hydrochloride,
8.410 parts of sodium dihydrogen citrate,
6.590 parts of sodium bicarbonate,
showed, after one week at 60° C., a 3.6% level of N-carbamyl-N'-methyl-N'-[2-(5-methyl-4-imidazolylmethylthio)ethyl]-guanidine.

In the same storage conditions, a mixture of
1.1445 parts of cimetidine hydrochloride,
4.320 parts of sodium dihydrogen citrate,
5.380 parts of disodium hydrogen citrate,
showing the same effervescent activity (62%) as the one of the couple obtained at the end of example 14 showed after one week at 60° C. a 3.2% level of N-carbamyl-N'-methyl-N'-[2-(5-methyl-4-imidazolylmethylthio)ethyl]-guanidine.

EXAMPLE 16

In a drier granulator blender comprising a thermostatable jacketed vessel connected to a vacuum pump, an aperture for charging solid materials, an aperture for introducing liquids in dispersed form, a mixing device assuring a thorough homogeneity and an atmospheric pressure outlet device and heated to 100° C., 36.750 kg of powdered anhydrous citric acid and 63.250 kg of sodium bicarbonate are introduced through a one millimeter opening grid sieve. The mixture is heated under vigorous stirring. When the temperature of the products reaches 40° C. (±1° C.), the thermostat of the jacket is set on 75° C. (±1° C.).

When the temperature of the mixture reaches 45°–46° C., and the temperature of the jacket is 75° C., pulverized water (160 ml) is added under vigorous stirring. The mixture is allowed to react for 28 minutes and 30 seconds. Stirring speed is then reduced and the reaction is stopped by drying under vigorous and continuous suction provoking a decrease of residual pressure and temperature (about 5° to 10° C.), this latter rising again as soon as the mass is dry.

Vacuum is then relieved and the mass is calibrated through a two millimeters opening grid sieve.

A couple (73.520 kg) with sodium bicarbonate in excess to the stoichiometric amount is obtained with a 61.9% effervescent activity and corresponding to a composition of 26.3% in sodium dihydrogen citrate, 25.7% in disodium hydrogen citrate and 48% in sodium bicarbonate.

EXAMPLE 17

In room conditions controlled for temperature (20° C.) and relative humidity (20%), cimetidine hydrochloride (1.445 part) is thoroughly mixed with 15 parts of the couple obtained at the end of Example 16 and the mixture is distributed into bags formed by sealing of Kraft complex sheets 50 g, polyethylene 12.5 g, aluminum 30 μm and polyethylene 25 g.

In order to test the stability of the so-packaged powder, bags have been stored for one week at 60° C. and, after that period, no degradation product has been detected by high performance liquid chromatography.

In the same storage conditions, a mixture of
1.1445 part of cimetidine hydrochloride
9.4875 parts of sodium bicarbonate
5.5125 parts of powdered anhydrous citric acid
showed after one week at 60° C. a 40.9% level of N-carbamyl-N'-methyl-N'-[2-(5-methyl-4-imidazolylmethylthio)ethyl]-guanidine and a 0.8% level of N-methyl-N'-[2-(5-methyl-4-imidazolylmethylthio)ethyl]-guanidine.

In the same storage conditions, a mixture of
1.445 part of cimetidine hydrochloride
6.97 parts of sodium dihydrogen citrate
8.03 parts of sodium bicarbonate
showed, after one week at 60° C. a 5.4% level of N-carbamyl-N'-methyl-N-[2-(5-methyl-4-imidazolylmethylthio)ethyl]-guanidine.

In the same storage conditions, a mixture of
1.445 part of cimetidine hydrochloride
3.94 parts of sodium dihydrogen citrate
3.86 parts of disodium hydrogen citrate
7.20 parts of sodium bicarbonate
showing the same activity (62.9%) as the one of the couple obtained at the end of example 16 showed after one week at 60° C. a 4.9% level of N-carbamyl-N'-[2-(5-methyl-4-imidazolylmethylthio)ethyl]-guanidine.

We claim:

1. A process for preparing an antacid effervescent couple wherein citric acid is mixed to an at least stoichiometric amount of alkali metal carbonate or bicarbonate and the homogenized mixture is granulated, characterized in that the mixture is allowed to react until a couple is obtained wherein citric acid is transformed in mono- and di-alkali metal citrate in a weight ratio comprised between about 8/1 and about 1/10, said reaction being stopped by drying under vigorous suction when from about 24% to about 54% of the potential amount of carbon dioxide is released.

2. A process for preparing an antacid effervescent couple according to claim 1 wherein weight ratio is comprised between about 2/1 and about 6/10.

3. A process for preparing an antacid effervescent couple according to claim 2 wherein sodium bicarbonate is used and wherein the mono- and di-alkali metal citrates are sodium dihydrogen citrate and disodium hydrogen citrate.

4. Antacid effervescent couple which comprises a mixture of sodium or potassium dihydrogen citrate and disodium or dipotassium hydrogen citrate within a weight ratio comprised between 8/1 and 1/10.

5. Antacid effervescent couple according to claim 4 wherein the weight ratio is comprised between about 2/1 and about 6/10.

6. An antacid effervescent couple according to claim 4 and wherein the citrates are sodium dihydrogen citrate and disodium hydrogen citrate.

7. Effervescent couple according to claim 4, which includes a lubricating agent which is a micronized benzoate.

8. Effervescent couple according to claim 7 wherein the micronized benzoate is siliconized sodium benzoate.

9. Pharmaceutical composition comprising an antacid effervescent couple according to claim 4 and an histamine $H_2$-antagonist with a non toxic pharmaceutically acceptable carrier.

10. Pharmaceutical composition according to claim 9 wherein the histamine $H_2$-antagonist is a derivative of cyanoguanidine.

11. Pharmaceutical composition according to claim 10 wherein the histamine $H_2$-antagonist derivative of cyanoguanidine is cimetidine in the form of free base or hydrochloride.

12. Pharmaceutical composition according to claim 9 wherein the composition is formulated in tablet form.

13. Pharmaceutical composition according to claim 9 wherein the composition is formulated in granule form.

14. Pharmaceutical composition according to claim 9 which also comprises an antacid.

15. Pharmaceutical composition according to claim 14 wherein the antacid is a carbonate or bicarbonate.

16. Pharmaceutical composition according to claim 15 wherein the antacid is sodium bicarbonate.

* * * * *